(12) United States Patent
Freese et al.

(10) Patent No.: US 9,109,107 B2
(45) Date of Patent: Aug. 18, 2015

(54) PEROXIDE COMPOSITION

(75) Inventors: Matthias Freese, Sassenberg (DE); Peter Hilzendegen, Insheim (DE); Frank Lauterwasser, Mannheim (DE); Reinhard Lorenz, Steinfurt (DE); Alexander Sokira, Gronau (DE); Johan Franz Gradus Antonius Jansen, Geleen (NL)

(73) Assignee: DSM IP ASSETS B.V., Heerlen (NL)

( * ) Notice: Subject to any disclaimer, the term of this patent is extended or adjusted under 35 U.S.C. 154(b) by 1170 days.

(21) Appl. No.: 12/746,293

(22) PCT Filed: Dec. 5, 2008

(86) PCT No.: PCT/EP2008/066902
§ 371 (c)(1),
(2), (4) Date: May 16, 2011

(87) PCT Pub. No.: WO2009/071670
PCT Pub. Date: Jun. 11, 2009

(65) Prior Publication Data
US 2014/0350167 A1 Nov. 27, 2014

(30) Foreign Application Priority Data
Dec. 6, 2007 (EP) .................................... 07023646

(51) Int. Cl.
| | | |
|---|---|---|
| *C07C 407/00* | (2006.01) | |
| *C07C 409/00* | (2006.01) | |
| *C08F 299/04* | (2006.01) | |
| *C08K 5/00* | (2006.01) | |
| *C08L 63/10* | (2006.01) | |
| *C08L 67/06* | (2006.01) | |
| *C08L 35/00* | (2006.01) | |
| *C08F 283/01* | (2006.01) | |
| *C08F 290/06* | (2006.01) | |
| *C08F 299/00* | (2006.01) | |
| *C08K 3/00* | (2006.01) | |
| *C08K 5/06* | (2006.01) | |
| *C08K 5/14* | (2006.01) | |
| *B29C 43/00* | (2006.01) | |
| *C08L 71/02* | (2006.01) | |
| *B29K 35/00* | (2006.01) | |
| *B29K 509/08* | (2006.01) | |

(52) U.S. Cl.
CPC ............... *C08L 35/00* (2013.01); *B29C 43/003* (2013.01); *C07C 407/006* (2013.01); *C08F 283/01* (2013.01); *C08F 290/062* (2013.01); *C08F 299/00* (2013.01); *C08F 299/04* (2013.01); *C08K 3/0033* (2013.01); *C08K 5/06* (2013.01); *C08K 5/14* (2013.01); *B29K 2035/00* (2013.01); *B29K 2509/08* (2013.01); *C07C 2101/08* (2013.01); *C08L 67/06* (2013.01); *C08L 71/02* (2013.01)

(58) Field of Classification Search
CPC ............ C07C 407/006; C07C 2101/08; C08F 283/01; C08F 290/062; C08F 299/00; C08F 299/04; C08K 3/0033; C08K 5/06; C08K 5/14; C08L 67/06; C08L 71/02
USPC ............... 525/11, 17, 55, 242, 244, 263, 265, 525/273, 383, 387; 568/567, 558; 252/186.26
See application file for complete search history.

(56) References Cited

U.S. PATENT DOCUMENTS

| | | | |
|---|---|---|---|
| 4,131,728 A | 12/1978 | Priddy | |
| 5,281,633 A * | 1/1994 | Okuno et al. | ............... 523/513 |
| 5,708,064 A | 1/1998 | Coleman et al. | |
| 2004/0094744 A1 | 5/2004 | Udding et al. | |
| 2006/0009598 A1 | 1/2006 | Stainbrook et al. | |

FOREIGN PATENT DOCUMENTS

| | | |
|---|---|---|
| EP | 1 621 567 | 2/2006 |
| GB | 1 334 289 | 10/1973 |
| JP | 8-157544 | 6/1996 |
| JP | 2002-105142 | 4/2002 |
| WO | WO 9833770 A1 * | 8/1998 |
| WO | WO 03/055946 | 7/2003 |
| WO | WO 2008125591 A1 * | 10/2008 |

OTHER PUBLICATIONS

International Search Report for PCT/EP2008/066902, mailed Mar. 4, 2009.
Database WPI Week 200254, Accession No. 2002-503515 & JP 2002-105142 (Apr. 10, 2002).
Database WPI Week 199634, Accession No. 1996-339231 & JP 08-157544 (Jun. 18, 1996).

* cited by examiner

*Primary Examiner* — Randy Gulakowski
*Assistant Examiner* — Christopher M Rodd
(74) *Attorney, Agent, or Firm* — Nixon & Vanderhye P.C.

(57) ABSTRACT

Peroxide compositions include an organic peroxide and a polyalkylene polyol, wherein the organic peroxide is an organic monoperoxycarbonate R—O—CO—O—O-tertiary butyl where R is a $C_1$-$C_6$ alkyl.

13 Claims, No Drawings

PEROXIDE COMPOSITION

The present invention relates to a peroxide composition comprising a peroxide. The present invention further relates to a process for radically curing an unsaturated polyester or vinyl ester resin composition using such peroxide composition. The present invention further relates to a two-component composition comprising at least a first component being a curable resin composition comprising an unsaturated polyester and/or vinyl ester and at least a second component comprising the peroxide composition, the two-component composition being suitable for use in sheet moulding compounds and bulk moulding compounds (SMCs and BMCs).

Curable resins in general, and unsaturated polyester resins and vinyl ester resins in particular, are useful in a variety of applications, including automotive parts. In a typical sheet moulding compound (SMC) or bulk moulding compound (BMC) used in the automotive industries the unsaturated polyester component usually represents about 10 to 15% by weight of the total formulation. SMC and BMC materials based on unsaturated polyester resins generally exhibit excellent physical properties, good surface appearance as well as good weather ability. The so-called Class A SMCs form a category of SMCs, as are preferably used in the automotive industries, that is particularly excellent in surface properties and, inter alia due to the presence of certain low profile additives, shows very good dimensional properties (shrinkage of from roughly −0.05% to −0.1% when being cured). They are generally applied in the production of car body parts or even complete car bodies. Notwithstanding these advantages, the unsaturated polyester or vinyl ester based composite materials according to the state of the art tend to exhibit a relatively high emission of volatile organic compounds (VOC).

Many approaches so far have been attempted to reduce the VOC-emissions of unsaturated polyester or vinyl ester based composite materials. For instance, reference can be made to attempts in changing the resin composition, use of a reactive diluent, and use of more active initiators for the polymerization reaction.

It has, for instance, as described in papers "Emissionen aus SMC/BMC Bauteilen", parts 1 & 2, from the "Arbeitsgemeinschaft Verstärkter Kunststoffe e.V.", 1997, turned out, that replacing commonly used peroxide initiators like t-butylperoxybenzoate (e.g. Trigonox® C, AKZO; the Netherlands) by other peroxide initiators such as peroxycarbonate initiators, for instance, t-butyl-peroxy 2-ethylhexyl carbonate (e.g. Trigonox® 117, AKZO; the Netherlands) or the like already leads to a major improvement in VOC-emissions by avoiding the formation of traces of benzene in the SMC/BMC-material. Accordingly, nowadays peroxycarbonates, in particular Trigonox 117, are considered to be the standard initiator in automotive SMC-parts.

A further reduction with respect to VOC is, however, urgently needed in order to comply with future environmental legislation for cars. Very demanding regulations in this respect are now in preparation, for instance, under the auspices of the Californian Air Resources Board (CARB). Reference can be made to an article ("Entwicklung HC emissionsoptimierter KFZ-Bauteile") of Frank, U. et al. in Kunststoffe im Automobilbau, Düsseldorf, VDI-Verlag, 2002. Car manufacturers will be forced to reduce any non-fuel emissions to lower levels and, therefore, they also will demand emission reductions from their suppliers for all automotive parts that are likely to contribute to VOC emissions. Accordingly, there is a strong industry need for providing moulded parts and in particular SMC- and BMC-parts having significantly reduced VOC emissions.

The inventors now found that a significant reduction of the VOC-emissions of in particular unsaturated polyester or vinyl ester based composite materials such as SMC and BMC parts can be achieved by using an organic monoperoxycarbonate R—O—CO—O—O-tertiary butyl where R is a $C_1$-$C_6$ alkyl. However, in view of the explosive nature of these peroxides, it is preferred to prepare or at least dilute such peroxide prior to its use in a phlegmatizer. Phlegmatizers, also known as diluents, are well known in the art and are useful for better processing, safety and the like.

A standard diluent used for incorporation into a peroxide initiator during manufacture or prior to its use is odorless mineral spirit (OMS), i.e. 1-dodecanol. A problem with the use of OMS is that it causes VOC emissions; see for example US 2006/0009598 which, for example, describes that OO-(t-butyl) O-isopropyl monoperoxycarbonate diluted in diethyl fumarate results in reduced VOC emission compared to dilution in odorless mineral spirit.

The problem with the use of such phlegmatizers, like 1-dodecanol and diethylfumarate, is that the surface quality and/or mechanical properties of parts obtained by moulding unsaturated polyester or vinyl ester based composite materials may be negatively affected.

The object of the present invention is to provide a peroxide/phlegmatizer combination that results after having cured a curable composition with such peroxide/phlegmatizer combination in a cured part with an exceptionally combination of good properties, in particular low VOC emission; good surface quality, i.e. low short term waviness (STW), low long term waviness (LTW), good homogeneity, high gloss and low amount of surface defects; good mechanical properties, i.e. flexural strength, outer fibre strain, flexular E-modulus and impact strength; and low smell.

This object is surprisingly achieved in that the peroxide is an organic monoperoxycarbonate R—O—CO—O—O-tertiary butyl where R is a $C_1$-$C_6$ alkyl and the peroxide composition further comprises a polyalkylene polyol. The polyalkylene polyol serves as phlegmatizer. The words phlegmatizer and diluents are used synonymously in this specification.

Thus, the peroxide composition according to the present invention can be used for preparing in particular unsaturated polyester or vinyl ester based composite materials such as SMC and BMC automotive parts having low total volatiles content while at the same time the surface properties of the moulded part, the smell and the mechanical properties remain good. The low volatiles content can be significantly reduced, but not at the expense of the Class A surface of the moulded part.

R is preferably a $C_1$-$C_5$ alkyl, more preferably a $C_1$-$C_4$ alkyl and even more preferably a $C_1$-$C_3$ alkyl.

Preferred organic monoperoxycarbonates are tertiarybutyl peroxy methyl carbonate, tertiarybutyl peroxy ethyl carbonate, tertiarybutyl peroxy propyl carbonate, tertiarybutyl peroxy isopropyl carbonate, tertiarybutyl peroxy butyl carbonate, tertiarybutyl peroxy isobutyl carbonate, tertiarybutyl peroxy tertiary butyl carbonate, tertiarybutyl peroxy cyclopentyl carbonate. A particular preferred organic monoperoxycarbonate is tertiarybutyl peroxy isopropyl carbonate.

The peroxide composition according to the invention comprises a polyalkylene polyol as phlegmatizer or diluent.

The polyalkylene polyol in the peroxide composition is a polymer or oligomer. Preferably, the molecular weight of the polyalkylene polyol in the peroxide composition is from 300 up to and including 5000 g/mol and more preferably from 400 up to and including 2000 g/mol. For the purposes of the invention, molecular weight means number average molecular weight as determined by gel permeation chromatography.

Preferably, the polyalkylene polyol contains polyether moieties. Polyalkylene polyol containing polyether moieties are for instance polymers like polyesters, polycarbonates or polyurethanes with polyether moieties like for instance polyethyleneoxide, polypropyleneoxide polytetrahydrofurane, polycyclohexeneoxide, ethylenoxide-propyleneoxide copolymer blocks, but also include polyethers like polyethylene oxide copolymers, polypropylene oxide copolymers, polytetrahydrofuran copolymers, copolymers of ethyleneoxide with cyclohexeneoxide as well as simple polyethers like polyethylene oxide, polypropylene oxide, polytetrahydrofuran.

Preferably the polyalkylene polyol is a polyether.

In one preferred embodiment, the polyalkylene polyol is a polyether with the formula HO—[—CHR—(CH$_2$)$_x$—O—]$_y$—H, in which R is hydrogen or methyl, x is an integer from 1 to 4, and y is an integer from 2-50.

According to another preferred embodiment the polyalkylene polyol is a polyalkylene glycol, preferably containing ethylene glycol moieties and/or propylene glycol moieties. More preferably the polyalkylene polyol is poly(1,2-propylene glycol). It has surprisingly been found that the peroxide of the peroxide composition according to the invention can advantageously be prepared in poly(1,2-propylene glycol). Preferably, poly(1,2-propylene glycol) having a molecular weight of from 300 to 5000 g/mol is used, more preferably of from 400 to 2000 g/mol and more preferably of from 700 to 1000 g/mol. Using poly(1,2-propylene glycol) having a molecular weight within this preferred range results in that the advantageous effects of the invention are even more pronounced.

Obviously mixtures of different polyalkylene polyols can be employed according to the invention.

In this invention the polyalkylene polyol is serving as a phlegmatizer or as a diluent for the monoperoxycarbonate. When looking from safety aspects the polyalkylene polyol reduce any unwanted reactivity of the peroxide (i.e. explosion by shock or flame supporting behaviour). Besides, it may be required by legislation (concerning explosives, safety of transport and storage) to reduce the active oxygen content below a certain limit. When looking with the eyes of an unsaturated polyester resin technologist, the polyalkylene polyol act as a diluent. Their special feature is that they do not have an adverse effect in the SMC/BMC process and also not on the performance of the SMC/BMC part and at the same time they do not contribute to volatile organic compounds (VOC) emission of the cured SMC/BMC part.

The minimum amount, required for safety reasons, of polyalkylene polyol in the peroxide composition according to the present invention depends on the kind of peroxide used and is in general at least 5 wt. %, mostly at least 10 wt. % (relative to the total peroxide composition). For example, for tertiary-butyl peroxy isopropyl carbonate, the amount of polyalkylene polyol is at least 23 wt. % (relative to the total peroxide composition). The maximum amount of polyalkylene polyol is not critical and is in general lower than 99 wt. % and mostly lower than 95 wt. % (relative to the total peroxide composition).

The aforementioned peroxides and their method of preparation are well known in the art. The dilutions of the peroxides can be effected at any convenient stage in the process, before, during and/or after their preparation. For safety reasons, the dilution of the peroxide is preferably effected before and/or during their preparation.

The present invention further relates to a process for radically curing an unsaturated polyester or vinyl ester resin composition, wherein the process comprises (i) combining an unsaturated polyester or vinyl ester resin composition with the peroxide composition of the present invention and then (ii) radically curing the resin composition. Preferably the curing process is effected by moulding at increased temperature, more preferably by compression moulding to obtain preferably a sheet moulding compound or bulk moulding compound.

The present invention further relates to a two-component composition comprising at least a first component being a curable resin composition comprising an unsaturated polyester and/or a vinyl ester and at least a second component comprising the peroxide composition of the invention. Preferably, the curable resin composition is a thermally curing composition. The curable resin composition preferably comprises (a) an unsaturated polyester or vinyl ester, (b) a monomer which will copolymerize with the unsaturated polyester or vinyl ester, and (c) fibrous reinforcement material. Optionally, also a low profile additive and/or a low shrink additive (d), a filler (e), a thickening agent (f), a mould release agent (g), a wetting agent (h) and/or a viscosity reducing agent (g) could be included. A man skilled in the art knows which ranges can be applied for the components of the curable resin composition of the present invention. Suitable ranges are: 5-35 wt % unsaturated polyester and/or vinyl ester, 25-75 wt % reactive monomer, 0-10 wt % low profile additive and/or low shrink additive, 0-55 wt % filler and 20-50 wt % fibrous reinforcement material (relative to the total resin composition).

Preferably, the thermally curable resin composition comprises (a) an unsaturated polyester or vinyl ester, (b) a monomer which will copolymerize with the unsaturated polyester and/or vinyl ester, and (c) fibrous reinforcement material, and (d) a low profile additive and/or a low shrink additive. More preferably, the thermally curable resin composition comprises (a) 5-35 wt % of an unsaturated polyester and/or a vinyl ester, (b) 25-75 wt % of a monomer which will copolymerize with the polyester or the vinyl ester, (c) 20-50 wt % fibrous reinforcement material and (d) 0.1-10 wt % a low profile additive and/or a low shrink additive.

In one embodiment of the invention, the thermally curable resin formulation is a simple structural formulations (not comprising low profile and low shrink additives but comprising fibrous reinforcements). In another and more preferred embodiment of the invention, the thermally curable resin composition is a low profile (LP) formulation or a low shrink (LS) formulation. (LP) formulations comprise a low profile additive and low shrink (LS) formulations comprises a low shrink additive. Low profile (LP) and low shrink (LS) additives are known to a person of ordinary skilled in the art. LP additives improve the surface smoothness or "profile" of SMC/BMC parts and reduce shrinkage during the curing of SMC/BMC parts. LS additives reduce shrinkage during the curing of SMC/BMC parts, but to a less extent than LP additives.

In still another and preferred embodiment of the invention, the thermally curable resin formulation is a class A SMC formulation. As meant herein, the term "shrink-controlled" reflects that the shrinkage of the resin composition upon curing, under both standard compression and injection moulding conditions, generally temperatures of 130 to 170° C. and pressures of 5 to 10 MPa, is in the range of from +1% to −0.1%. Within said broadest range, narrower sub-ranges can be distinguished. The skilled man in the field usually defines such ranges and sub-ranges, as (i) low-shrink (also referred to as LS; this is the broadest range of shrinkage, ranging from roughly +1% to +0.2% shrinkage upon curing);
(ii) low-profile (also referred to as LP; this is the range of shrinkage from roughly +0.2% to −0.05% shrinkage upon curing);
(iii) class A (this is the narrowest range of shrinkage, ranging from roughly −0.05% to −0.1% shrinkage upon curing).

It is to be noticed, that negative values of shrinkage correspond to (slight) expansion. There exists a vast amount of literature regarding shrinkage of unsaturated polyester resins, use of LPAs for shrinkage control, and mechanisms of shrinkage. Reference, for instance can be made to the following literature:

Atkins, K. E., in Paul D. R. and Newman S., editors, Polymer blends, Vol. 2, New York, Academic Press (1978), p. 391;
Han, C. D. et al., in J. Appl. Polym. Sci., 28 (1983), p. 743;
Meyer, R. W., Handbook of pultrusion technology, New York, Chapman and Hall (1988), p. 62.

The unsaturated polyester resin or vinyl ester resin used in the context of the present invention may be any such resin as is known to the skilled man. Examples thereof can be found in a review article of M. Malik et al. in J.M.S.—Rev. Macromol. Chem. Phys., C40 (2&3), p. 139-165 (2000). The authors describe a classification of such resins—on the basis of their structure—in five groups:

(1) Ortho-resins: these are based on phthalic anhydride, maleic anhydride, or fumaric acid and glycols, such as 1,2-propylene glycol, ethylene glycol, diethylene glycol, triethylene glycol, 1,3-propylene glycol, dipropylene glycol, tripropylene glycol, neopentyl glycol or hydrogenated bisphenol-A. Commonly the ones derived from 1,2-propylene glycol are used in combination with a reactive diluent such as styrene.

(2) Iso-resins: these are prepared from isophthalic acid, maleic anhydride or fumaric acid, and glycols. These resins may contain higher proportions of reactive diluent than the ortho resins.

(3) Bisphenol-A-fumarates: these are based on ethoxylated bisphenol-A and fumaric acid.

(4) Chlorendics: are resins prepared from chlorine/bromine containing anhydrides or phenols in the preparation of the UP resins.

(5) Vinyl ester resins: these are resins, which are mostly used because of their hydrolytic resistance and excellent mechanical properties, as well as for their low styrene emission; that have unsaturated sites only in the terminal position, introduced by reaction of epoxy resins (e.g. diglycidyl ether of bisphenol-A, epoxies of the phenolnovolac type, or epoxies based on tetrabromobisphenol-A) with (meth)acrylic acid. Instead of (meth)acrylic acid also (meth)acrylamide may be used.

Besides these classes of resins also so-called pure maleic resins and so-called dicyclopentadiene (DCPD) resins can be distinguished. Pure maleic resins (such as Palapreg P 18-21, Palapreg 0423-02, and Palapreg P18-03 of DSM Composite Resins, Schaffhausen, Switzerland) can very suitably be used in the context of the present invention. The same is true for all structural UP-resins and VE-resins with glass transition temperatures of the cured resins above 100° C. As used herein, pure maleic resins means that the diacid that is used for preparing the unsaturated polyester is maleic acid, maleic anhydride and/or fumaric acid. As used herein, a vinyl ester resin is a (meth)acrylate functional resin. Besides the vinyl ester resins as described in Malik et al., also the class of vinyl ester urethane resins (also referred to urethane methacylate resins) can be distinguished.

The monomer which will copolymerize with the unsaturated polyester or vinyl ester resin compositions according to the invention generally has the function of a cross-linking agent and/or a diluent. Examples of suitable monomers are, for instance, alkenyl aromatic monomer such as for example styrene and divinylbenzene but all other reactive monomers for use in the field of thermosetting resins as are known to the skilled man can be used. Preferred monomers are styrene, alpha-methyl styrene, chlorostyrene, vinyl toluene, divinyl benzene, methyl methacrylate, tert.butyl styrene, tert.butylacrylate, butanediol dimethacrylate and mixtures thereof.

Preferably the curable resin in the resin composition is an unsaturated polyester and more preferably a pure maleic resin.

Low profile additives (LPAs) and low shrink additives (LSAs) are well known to the skilled man in the field of thermosetting resins. Examples of suitable LPAs and LSAs are polyvinyl acetates, polymethyl methacrylates and copolymers with other acrylates, vinyl chloride—vinyl acetate copolymers, polyurethanes, styrene-butadiene copolymers and other elastomers, polystyrene and some copolymers, polycaprolactones, cellulose acetate butyrate, and a variety of saturated polyesters and blends of saturated polyesters with polyvinylchloride, etc. Examples of suitable additives include Palapreg H892-02 (a saturated polyester resin, LPA, DSM), Palapreg H814-01 (a polystyrene resin, LSA, DSM), Palapreg H1080-01 (a polyvinylacetate, LPA, DSM), LP40A (a polyvinylacetate, LPA,), and LP 138-46 (a polyurethane, LPA, Ashland). However, in the class A SMC formulations according to the invention, preferably LPAs are used that have been modified by chemically attaching thereto an uretdione diisocyanate. Such LPAs, prepared from standard LPAs with groups that are reactive with the uretdione diisocyanate (for instance, Palapreg H 892-02 and Palapreg H 2681-01 of DSM Composite Resins, Schaffhausen, Switzerland), are herein also referred to as LPAs functionalized with an uretdione diisocyanate.

Examples of suitable fibrous reinforcement material include glass fibres, carbon fibres, cellulose fibres and synthetic organic fibers such as polyethylene, polycarbonates, polyamides and mixtures thereof. It is particularly preferred, that the fibrous reinforcement material in the resin compositions according to the present invention consists of glass fibers.

Examples of suitable fillers are alumina trihydrate, alumina powder, aluminosilicate, barium sulphate, calcium carbonate, calcium sulphate, clay, dolomite, hollow glass spheres, limestone dust, mica, quartz powder, crushed silica, talc and mixtures thereof.

Examples of suitable thickening agents include MgO, $Mg(OH)_2$ and potentially CaO. Preferred thickening agents include MgO and $Mg(OH)_2$.

Examples of suitable release agents include zinc stearate, calcium stearate and mixtures of both, and processing additives from Byk Chemie like for example Byk P9080 and Byk P9050.

Examples of suitable wetting agents include Byk W9010 from Byk Chemie.

The present invention also relates to parts obtained by curing of a curable resin composition as defined herein with a peroxide composition according to the invention. Preferably, the curing is effected by moulding, more preferably the curing is effected by compression moulding to obtain in particular a SMC or BMC part. Preferably the curing is effected in such a way that the SMC or BMC part has class A surface.

According to one embodiment of the invention the curing is effected thermally, preferably at a temperature that is at least 130° C., and more preferably at least 140° C.; the temperature is preferably at most 170° C. more preferably at most 160° C. The present invention in particular relates to a SMC or BMC part obtained by thermally curing a two component composition according to the invention in a SMC or BMC mould, preferably the thermally curing is effected at a temperature of at most 170° C.

It should also be noted that the peroxide composition of the invention can advantageously be used for curing in-mould coatings. In-mould coatings are used to reduce the number of surface defects such as for example pinholes, blowouts, and surface cracks on the surface of the SMC or BMC part. Beside that in-mould coating can be used to make the surface conductive.

The invention is now being demonstrated by means of a series of examples, but is not restricted in any way to the embodiments shown in the examples.

EXAMPLES AND EXPERIMENTS

Experimental Section

The resin formulations were cured in a mould at 148° C. (patrix mould-half)/155° C. (matrix mould-half) during 120 seconds under 100 bar pressure. After demoulding, the so obtained parts were thermally post treated in an oven during 30 min at 190° C. to simulate the process of cataphoretically painting. After cooling to room temperature, the surface quality of the so obtained parts was determined via visual inspection. In this visual inspection the surface was inspected for long waviness (LTW), short waviness (STW), the homogeneity of the surface, the gloss of the surface, if the reinforcing fibres showed print through and the amount of surface defects. The mechanical properties were determined according to ISO 178 employing a Frank 81105 test equipment.

Shrinkage was determined as linear shrinkage using a precision measuring unit Electronic Scale from Time Electronic.

The VOC was determined according to VDA 278 using a Gerstel TDS incl. Autosampler, a Gerstel "Kaltaufgabesystem" KAS 4, a GC Hewlett-Packard 6890 equipped with a Mass Selective Detector "MS" Hewlett-Packard 5973.

Smell was determined according to VDA 270.

Examples 1-3 and Comparative Examples A-H

Formulations were prepared based on 57 parts unsaturated polyester (Palapreg P18-03 of DSM Composite Resins, Schaffhausen, Switzerland, 65% resin in styrene), 33 parts saturated polyester (H2681 of DSM Composite Resins, Schaffhausen, Switzerland, 70% resin in styrene), 10 parts polyvinylacetate solution (40% in styrene), 3 parts styrene containing some inhibitor (in order to tune the gel time in the operating window), 1 part peroxide (type shown in the table), 210 parts calcium carbonate (filler; of Millicarb, Omya, UK), 4 parts calcium stearate (mould release agent), 3.2 parts viscosity reducers (2.2 parts Byk W9010 of BYK and 1 part VR3 of DOW), 2.5 parts phlegmatizer (see table), 2.2 part magnesium oxide and 97 parts glass reinforcements with a length of 26 mm (P204 of Vetrotex, France).

After moulding and post cure the properties of the parts were determined. In the table the following abbreviations are used:
B=t-butyl peroxy isopropyl carbonate (BIC) (70% in pluriol P 900)
T=Trigonox 117 (t-butyl peroxy 2-ethylhexyl carbonate)

The examples and comparative experiments, in which a wide range of phlegmatizers has been evaluated, clearly demonstrate that a good surface quality combined with low emissions, low smell and good mechanical properties can only be obtained with the combination according to the invention.

TABLE 1

| | Example/Comparative Experiments | | | | | | | | | | |
|---|---|---|---|---|---|---|---|---|---|---|---|
| | 1 | 2 | 3 | A | B | C | D | E | F | G | H |
| Peroxide | B | B | B | B | B | B | B | B | B | B | T |
| Phlegmatizer | Pluriol P900 (PPG-900 of BASF) | Pluriol E400 (PEG-400 of BASF) | Pluriol E1000 (PEG-1000 of BASF) | Tricresyl phosphate | Nipol 1312 (liquid nitrile rubber of Zeon Chemical) | Adipic polyester (H892 of DSM) | 1-dodecanol | Epoxidized soy bean oil (Lankroflex E2307 of Akcros, UK) | Paraffin oil | Diethyl fumarate (of Merck) | None |
| LTW* | 2 | 2 | 2 | 2 | 4 | 2 | 2 | 2 | 3.5 | 2 | 2 |
| STW* | 2 | 2.5 | 2 | 2 | 3 | 4 | 3.5 | 3.5 | 3 | 4.5 | 4 |
| Homogeneity* | 2 | 2 | 2.5 | 2 | 2 | 4 | 2 | 2 | 5 | 3 | 2 |
| Gloss* | 2.5 | 2.5 | 2.5 | 2.5 | 2.5 | 2.5 | 2.5 | 1.5 | 4 | 2.5 | 2.5 |
| Fiber print through* | 2.5 | 2.5 | 2.5 | 3 | 3.5 | 4.5 | 3.5 | 4 | 5 | 6 | 4 |
| Defects* | 1 | 1 | 1 | 3 | 2 | 5 | 3 | 4 | 4 | 3 | 1 |
| Defect type | | | | | | Few blisters | Few blisters | Blisters | Blisters | Blisters | |
| Flex strength (MPa) | 119 | 134 | 138 | 131 | 124 | 123 | 125 | 130 | 123 | 139 | 125 |
| Outer fiber strain (%) | 2.01 | 2.08 | 2.06 | 2.07 | 2.1 | 1.99 | 2 | 1.97 | 1.94 | 2.06 | 1.97 |
| Flexural E-modulus (GPa) | 9.8 | 10.5 | 10.5 | 10.5 | 9.4 | 10.2 | 10.1 | 10.2 | 10.2 | 11 | 10.3 |
| VOC | 146 | 154 | 129 | 203 | 129 | 101 | 1226 | 152 | 156 | 124 | 283 |
| Smell | 3.75 | 4 | 4.25 | 4.25 | 6 | 4.75 | 4.5 | 4.25 | 3.75 | 4.75 | 5 |
| Shrinkage | −0.1107 | −0.1164 | −0.0933 | −0.0813 | −0.091 | −0.097 | −0.1104 | −0.1022 | −0.0873 | −0.0821 | −0.1007 |

*1 = good, 6 = bad

Example 4 and Comparative Experiments I-L

For safety reasons, it is preferred to prepare t-butyl peroxy isopropyl carbonate BIC in a phlegmatizer because pure BIC is a very explosive peroxide. In these experiments BIC phlegmatizer combinations were evaluated in which the BIC was prepared in the phlegmatizer.

Formulations were prepared based on 57 parts unsaturated polyester (P18-03, 65% resin in styrene), 33 parts saturated polyester (H2681, 70% resin in styrene), 10 parts polyvinylacetate solution (40% in styrene), 3 parts styrene containing some inhibitor, 1 part peroxide solution (table 2), 210 parts calcium carbonate (Millicarb), 4 parts calciumstearate, 3.2 parts release agents/viscosity reducers (2.2 parts Byk W9010 and 1 part VR3), 2.2 part magnesium oxide and 91 parts glass reinforcements with a length of 26 mm (P204).

After moulding and post cure, the properties of the parts were determined.

TABLE 2

|  | 4 | I | J | K | L |
| --- | --- | --- | --- | --- | --- |
| Peroxide | 70% BIC in Pluriol P900 | 70% BIC in epoxidized soy bean oil | 70% BIC in tricresyl phosphate | 70% BIC in diethyl fumarate | 70% T in Pluriol P900 |
| LTW | 2.5 | 2.5 | 2.5 | 2.5 | 2.5 |
| STW | 4 | 5 | 4 | 4.5 | 4 |
| Homogeneity | 3.5 | 3.5 | 3 | 4.5 | 3.5 |
| Gloss | 3.5 | 3.5 | 3.5 | 3.5 | 3.5 |
| Fibre print through | 2.5 | 2.5 | 2.5 | 2.5 | 2.5 |
| Defects | 1 | 1 | 2 | 1 | 1 |
| Flexural strength (MPa) | 130 | 128 | 130 | 135 | 128 |
| Outer fibre strain (%) | 2.08 | 2.03 | 2.04 | 2.05 | 2 |
| Flexural E-modulus (GPa) | 10.6 | 10.6 | 10.8 | 11 | 10.5 |
| Impact strength (kJ/m2) | 94 | 95 | 91 | 102 | 94 |
| VOC | 123 | 152 | 135 | 205 | 269 |
| Smell | 4 | 3.8 | 4.7 | 3.5 | 4.7 |
| Shrinkage | −0.060 | −0.066 | −0.061 | −0.072 | −0.075 |

The results in this table demonstrate that the best overall performance can only be obtained with the peroxide/phlegmatizer combination according to the invention. Comparing example 4 with comparative experiment L clearly shows the improvement especially in emissions and smell of BIC in Pluriol P900 compared to T in Pluriol P900. It also shows that the use of BIC in Pluriol P900 compared to the use of BIC in other phlegmatizers (Example 4 compared to Comparative Experiments I-K) shows that the use of BIC in Pluriol P900 results in an improvement in VOC emission, but also in better surface quality. Furthermore, it should be noted that tricrecyl phosphate is harmful for the environment and therefore also not preferred to be used.

The invention claimed is:

1. A peroxide composition comprising
   i) tertiarybutyl peroxy isopropyl carbonate; and
   ii) a polyalkylene polyol selected from the group consisting of 1,2-polypropylene glycol and polyethylene glycol that acts as a diluent for the organic monoperoxycarbonate, wherein
   the polyalkylene polyol is an oligomer or polymer having a number average molecular weight as measured by gel permeation chromatography from 400 up to and including 2000 g/mol, and wherein
   the polyalkylene polyol is present in an amount of at least 23 and lower than 95 wt. % relative to total weight of the peroxide composition.

2. A process for radically curing an unsaturated polyester or vinyl ester resin composition comprising
   (i) combining an unsaturated polyester or vinyl ester resin composition with a peroxide composition according to claim 1; and then
   (ii) radically curing the resin composition.

3. The process according to claim 2, wherein the curing is effected by moulding at increased temperature.

4. The process according to claim 3, wherein the moulding is compression moulding.

5. A two-component composition comprising at least a first component being a curable resin composition comprising an unsaturated polyester and/or vinyl ester and at least a second component comprising a peroxide composition according to claim 1.

6. The two-component composition according to claim 5, wherein the curable resin composition is a thermally curable resin composition comprising:
   (a) 5-35 wt % of an unsaturated polyester and/or a vinyl ester,
   (b) 25-75 wt % of a monomer which will copolymerize with the polyester or the vinyl ester,
   (c) 20-50 wt % fibrous reinforcement material, and
   (d) 0.1-10 wt % a low profile additive and/or a low shrink additive.

7. A part obtained by curing a peroxide composition according to claim 1 with a curable resin composition.

8. A cured part comprising a cured composition according to claim 5.

9. The cured part according to claim 8, wherein curing is effected by compression moulding.

10. A cured part comprising a cured composition according to claim 6.

11. A cured part comprising a cured composition according to claim 7.

12. A cured part obtained by the process according to claim 3.

13. A cured part obtained by the process according to claim 4.

* * * * *